US010076402B2

United States Patent
Grewe

(10) Patent No.: US 10,076,402 B2
(45) Date of Patent: Sep. 18, 2018

(54) VASCULAR FILTER WITH PRESSURE SENSOR AND VALVE

(71) Applicant: Cook Medical Technologies LLC, Bloomington, IN (US)

(72) Inventor: David D. Grewe, Grand Junction, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 338 days.

(21) Appl. No.: 14/741,763

(22) Filed: Jun. 17, 2015

(65) Prior Publication Data

US 2015/0374480 A1    Dec. 31, 2015

Related U.S. Application Data

(60) Provisional application No. 62/017,512, filed on Jun. 26, 2014.

(51) Int. Cl.
| | | |
|---|---|---|
| *A61F 2/01* | (2006.01) | |
| *A61M 39/24* | (2006.01) | |
| *A61B 5/0215* | (2006.01) | |
| *A61F 2/24* | (2006.01) | |

(52) U.S. Cl.
CPC ............. *A61F 2/01* (2013.01); *A61B 5/0215* (2013.01); *A61B 5/02158* (2013.01); *A61B 2562/0247* (2013.01); *A61F 2/2475* (2013.01); *A61F 2250/0098* (2013.01); *A61M 2205/04* (2013.01); *A61M 2210/12* (2013.01)

(58) Field of Classification Search
CPC .......... A61F 2/01; A61F 2/013; A61F 2/2475; A61F 2002/011; A61F 2002/015–2002/018
See application file for complete search history.

(56) References Cited

U.S. PATENT DOCUMENTS

| | | | |
|---|---|---|---|
| 8,103,361 | B2 | 1/2012 | Moser |
| 8,251,067 | B2 | 8/2012 | Hendricksen et al. |
| 8,267,954 | B2 | 9/2012 | Decant, Jr. et al. |
| 8,613,753 | B2 | 12/2013 | Angel et al. |
| 2002/0165575 | A1 | 11/2002 | Saleh |

(Continued)

FOREIGN PATENT DOCUMENTS

WO    WO 2009/123715    10/2009

OTHER PUBLICATIONS

Medgadget.com, "Perminova Aims to Monitor Chest Fluid for Early Detection of Heart Failure and Other Diseases", posted by Editors on Feb. 26, 2014, Cardiac Surgery, Cardiology, Critical Care, Medicine, Thoracic Surgery, http://www.medgadget.com/2014/02/perminova.html/print/.

*Primary Examiner* — Shaun L David
(74) *Attorney, Agent, or Firm* — Woodward, Emhardt, Moriarty, McNett & Henry LLP

(57) ABSTRACT

Systems and devices with an implantable, intravascular filter for preventing emboli from traveling into brain and causing a stroke or transient ischemic attack are disclosed. In particular, an implantable, intravascular device having a filter element, a pressure sensor, and a valve is disclosed. The valve is biased into a closed configuration and changes into an open configuration upon a predetermined pressure drop across the filter. Systems comprising an external device at least one implantable device are also disclosed.

21 Claims, 4 Drawing Sheets

(56) References Cited

U.S. PATENT DOCUMENTS

| | | | |
|---|---|---|---|
| 2009/0105813 A1* | 4/2009 | Chambers | A61F 2/2412 623/2.12 |
| 2011/0313446 A1 | 12/2011 | Lambrecht et al. | |
| 2012/0277855 A1* | 11/2012 | Lashinski | A61F 2/2436 623/2.18 |
| 2013/0197621 A1 | 8/2013 | Ryan et al. | |

* cited by examiner

VASCULAR FILTER WITH PRESSURE SENSOR AND VALVE

FIELD OF THE DISCLOSURE

The present disclosure relates to medical devices, systems and methods. More particularly, the present disclosure relates to devices, systems and methods for use in preventing embolic material from blocking an artery that supplies blood to the brain.

BACKGROUND

Strokes are a leading cause of death and paralysis in the world. A stroke occurs when an artery that carries blood to the brain is blocked (i.e., occluded) or ruptures. The blockage or rupture causes reduced blood flow to portions of the brain which results in portions of the brain becoming starved for oxygen or nutrients. If revascularization (i.e., restored blood flow) does not occur, necrosis of brain cells will result.

Blockages that result in strokes are often caused by a blood clot (i.e., thrombus), fatty deposit (i.e., plaque) or other emboli that becomes lodged within the blood vessel. Total occlusions or partial occlusions (i.e., stenosis) are often the result of diseases of the arterial wall. Arterial atherosclerosis is by far the most common arterial disorder and when complicated by thrombosis or embolism it often is the most frequent cause of cerebral ischemia and infarction, resulting in cerebral stroke. Stroke caused by heart disease is primarily due to embolism by thrombotic material forming on the arterial or ventricular wall or the left heart valves. These thrombi can then detach and embolize into the arterial circulation.

Endarterectomy, angioplasty and carotid stenting are procedures targeted at opening an occluded artery; however, they do not prevent progression of new plaque. Even more so, the above treatment methods only provide a solution to localized problems and do not prevent proximal embolic sources, i.e., embolus occurring at remote sites (heart and ascending aorta) to pass through the reopened stenosis in the carotid and occlude smaller arteries in the brain. This is a substantial problem, inasmuch as about one-third of patients suffering from carotid occlusion also have proximal embolic sources leading to stroke.

Introducing filtering means into blood vessels, in particular into veins, has been known for some time. However, filtering devices known in the art often become clogged and need to be cleaned or replaced. When considering the possible cerebral effects of even fine embolic material occluding an artery supplying blood to the brain, the consequences may be fatal or may cause irreversible brain damage. In light of the short period of time during which brain tissue can survive without blood supply, there is a need for improvement in this field.

SUMMARY

The present disclosure describes devices and systems directed to preventing an ischemic event in the brain of a patient, such as a stroke or a transient ischemic attack. In particular, the present disclosure provides devices and systems having an implantable, intravascular filter that catches and prevents emboli from traveling into the brain of a patient. These devices and systems also include at least one valve that can allow increased blood flow through a filter and at least one pressure sensor that can notify a patient or medical care professional of the condition of the implanted filter. In some embodiments, an implantable device for implantation into a blood vessel of a patient, comprises a filter having a first filter element with an upstream side and a downstream side and defining a plurality of filter passageways extending from the upstream side to the downstream side; a pressure sensor coupled to the filter and in communication with blood adjacent to the downstream side when the filter is implanted in a blood vessel; and a valve coupled to the filter and extending across a portion of the downstream side of the first filter element and configurable from a closed configuration to an open configuration; wherein in the closed configuration the valve member closes openings of some of the plurality of filter passageways; and wherein the valve is biased into the closed configuration.

In some instances, the filter has a maximum outer dimension of 4 to 15 millimeters. More preferably, depending on the vessel in which the implantable device is being implanted, the filter has a maximum outer dimension of 6 millimeters. Additionally or alternatively, the valve can comprise a check valve and/or the valve can comprise a valve member that is arranged to move into the open configuration when the fluid pressure on the upstream side is at least 1300 or 7000 Pascals greater than the fluid pressure on the downstream side of the first filter element. In certain embodiments, the valve is a flap valve or a duckbill valve.

The pressure sensor can be a differential pressure sensor that is also in communication with fluid adjacent to the upstream side of the filter element when the filter element is implanted in a patient so that the pressure sensor outputs a signal that corresponds to the pressure difference between fluid adjacent the upstream side and fluid adjacent the downstream side of the filter element. Some embodiments also include a second pressure sensor coupled to the first filter element and in communication with fluid adjacent to the upstream side of the first filter element; wherein the first and second pressure sensors are sealed pressure sensors and measure pressure within the blood vessel relative to a fixed pressure within the sensor.

The present disclosure also describes systems, comprising a first implantable device having the implantable device of any implantable device of this disclosure; and an external device in wireless communication with the pressure sensor of the first implantable device. Additionally, the systems can include a second implantable device; wherein the external device is in wireless communication with the pressure sensor of the second implantable device.

The external device can have one or more alarms triggerable by at least a signal output of the pressure sensor of the first implantable device, and additionally or alternatively, the external device can have a wireless power unit arranged to power at least the first implantable device. In some instances, the wireless power unit comprises a radio-frequency transmitter; and the first implantable device comprises a radio-frequency receiver.

It should be appreciated, that concepts and features illustrated and/or described in some embodiments are not intended to be limited to only those embodiments, unless otherwise stated. In other words, it is contemplated that features described with some embodiments may be substituted for or combined with features illustrated in other embodiments. Similarly, the illustrated and described embodiments are not intended to be limited to only the combination of features illustrated.

Further forms, objects, features, aspects, benefits, advantages, and embodiments of the present disclosure will become apparent from a detailed description and drawings provided herewith.

DESCRIPTION OF THE ILLUSTRATED EMBODIMENTS

Figure 1:
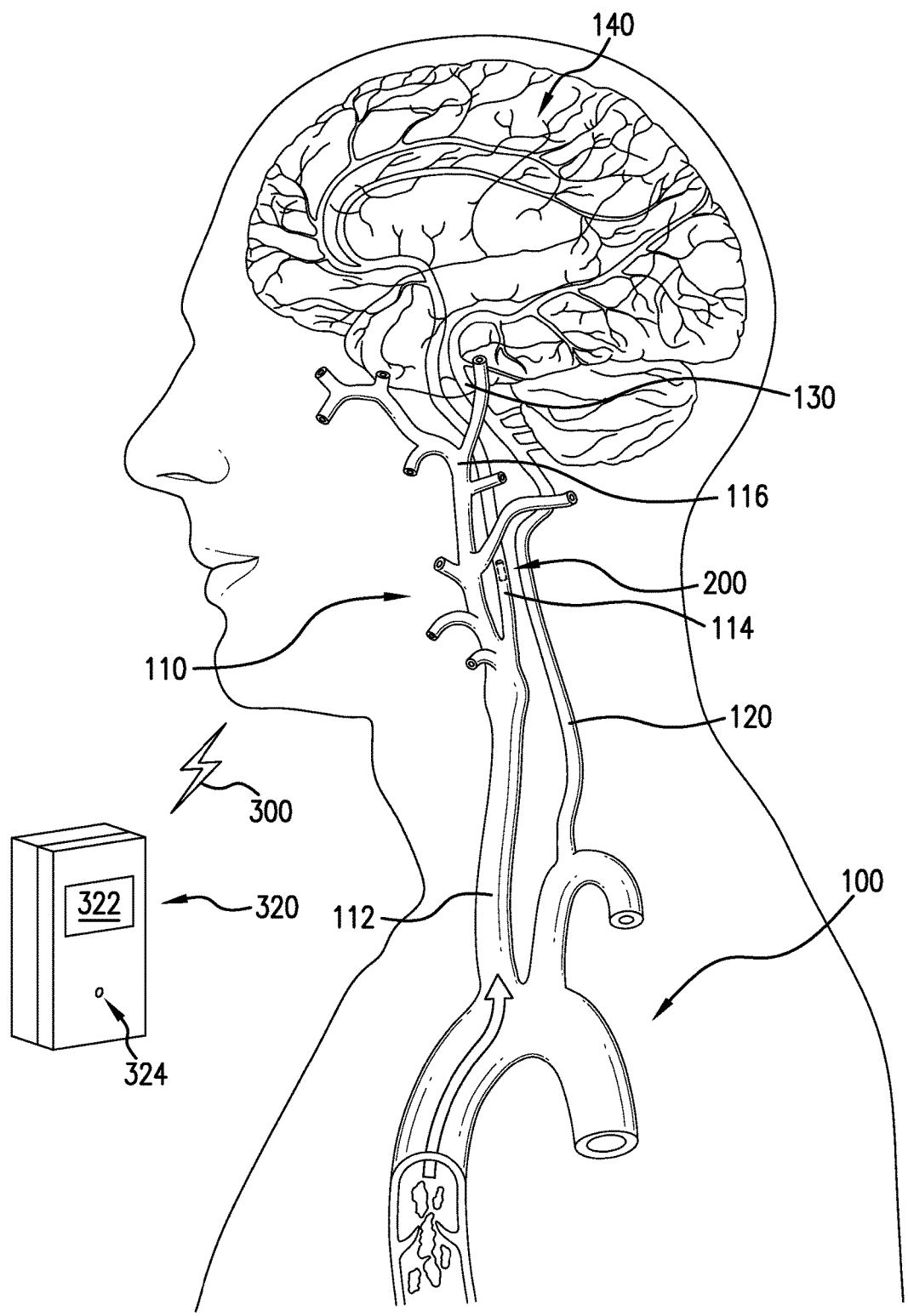
FIG. 1 illustrates an exemplary system in association with a side view of a patient's vasculature in the head, neck, and upper chest.

For the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which the disclosure relates.

The accompanying figures show mere examples of that which is claimed. Those examples are described here. As used in the claims and the specification, the following terms have the following defined meanings:

The term "thrombus" means a clot in the cardiovascular system formed during life from constituents of blood.

The term "embolus" means a plug composed of a detached thrombus or other material that occludes a blood vessel.

The term "alarm" means an electrical or mechanical device that emits energy such as sound or light as a warning signal.

The term "blood" means the fluid in the body of a human or an animal that contains white and red blood cells. It can also include platelets, plasma, proteins and metabolic by-products.

The term "blood vessel" means the tubes in the body of a human or an animal that carry blood to and from tissues and organs.

The term "check valve" means a valve that permits the flow of fluid in primarily a one-way direction. If the fluid flow is opposite the direction of flow allowed by the valve, the valve will close or remain closed and block the flow of fluid. Conversely, if the fluid flow is in the direction of the flow allowed by the valve, the valve will open or remain open and allow the fluid to pass.

The term "coupled" means joined or linked together. It includes but is not limited to objects that are moveable with respect to one another (e.g., pivotable, slidable, and/or rotatable) and objects that are fixed in relation to one another either permanently or temporarily in the environment in which they are intended to operate.

The term "differential pressure sensor" means a pressure sensor that measures the pressure of one fluid relative to the pressure of another fluid (i.e., the reference fluid) that is not fixed within the sensor.

The term "distal" means away from the operator during use (typically a surgeon), relative to its opposite: proximal.

The term "downstream side" means the side of the object that faces downstream in the blood vessel after positioning in the desired orientation within the body of a human or an animal.

The term "duckbill valve" means a valve comprising a flexible material, such as a rubber or synthetic elastomer, that is formed into a shape, such as a tube, that defines an inner passageway and has at an end of the passageway open and another end of the passageway being closed by the sides of the passageway being brought into abutting contact with another.

The term "external device" means a device located outside of the skin of the body of the patient.

The term "flap valve" means a valve that comprises a hinged plate that can swing from an open configuration to a closed configuration.

The term "fixedly coupled" means joined or linked together in fixed relation (i.e., not pivotable, slidable, or rotatable) relative to one another either permanently or temporarily in the environment in which they are intended to operate.

The term "filter passageway" means an empty space extending between an upstream opening and a downstream opening of a filter element. The filter passageway can connect to one or more upstream openings and one or more downstream openings. The filter passageways and the openings connected thereto can vary in size from one another and can vary in size relative to other passageways and openings.

The term "filter element" means a porous member through which blood is passed to separate out emboli. The porous member can comprise a plurality of intersecting strands or a material that defines a plurality of openings and passages there through (either naturally or by processing).

The term "maximum outer dimension" means the greatest dimension as measured across the object or feature from an outer surface to an opposing outer surface. The maximum outer dimension includes but is not limited to an outside diameter of a circular object or feature.

The term "opening" means a portion of a surface either substantially absent of material and/or which is adapted to be filled with, or at least receive, some other material, such as for example a drug formulation. Examples of openings include but are not limited to gaps, holes, apertures, wells, divots, and/or channels.

The term "portion" means a part of. It includes but is not limited to something less than the whole.

The term "pressure sensor" means a device that responds to the pressure or changes in pressure of a substance and is useful for measuring the pressure of the substance. The device can be a mechanical, electrical, and/or chemical device and can be any one of a variety of types of pressure sensors. For example, the pressure sensor can be of the force collector type such as a piezoresistive strain gauge, capacitive, electromagnetic, piezoelectric, optical, potentiometric, or triboluminescent. Alternatively, the pressure sensor can be of the resonant, thermal, or ionization type. The pressure sensor can be a differential pressure sensor that measures the difference between two substances in communication with the sensor or a sealed pressure sensor that measures pressure relative to some fixed pressure; however, other types of pressure sensors could be used as well.

"Passive sensor" means a sensor that has no intrinsic power source itself but receives energy from some outside source and uses this energy to transmit a signal to an external receiver.

The term "proximal" means toward the operator during use (typically a surgeon), relative to its opposite: distal.

The term "radio-frequency transmitter" means a device that transmits radio waves and includes transmitters and transceivers. The term includes but is not limited to devices that transmit low frequency (30-300 KHz), medium frequency (300 KHz-3 MHz), high frequency (3-30 MHz), very high frequency (30-300 MHz), ultra high frequency (300 MHz-3 GHz), and super high frequency (3-30 GHz) radio waves.

The term "radio-frequency receiver" means a device that receives radio waves and includes transceivers. The term includes but is not limited to devices that receive low frequency (30-300 KHz), medium frequency (300 KHz-3 MHz), high frequency (3-30 MHz), very high frequency (30-300 MHz), ultra high frequency (300 MHz-3 GHz), and super high frequency (3-30 GHz) radio waves.

The term "wireless communication" means communication free of mechanical connections. For example, the term includes but is not limited to communication via radio frequency, infrared, and ultrasound transmissions.

The term "wireless power unit" means a device capable of providing power to another device through wireless transmission. It can include but is not limited to a device capable of generating magnetic fields, electro-magnetic fields and/or light to another device which can then use the field and/or light to generate electricity.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The term "and/or" means, inclusively, both "and" (conjunctively) as well as "or" (disjunctively).

Referring now to the provided figures, FIG. 1 illustrates a side view of the head, neck, and chest of a patient and shows the aortic arch 100, carotid arteries 110, vertebral artery 120, basilar artery 130, and cerebral arteries 140. The implantable devices described and illustrated in the following embodiments can be positioned in the common carotid artery 112, the internal carotid artery 114, the external carotid artery 116, the vertebral artery, or the basilar artery. For example, the implantable device 200 described herein can be positioned within the internal carotid artery of a patient.

Figure 2:
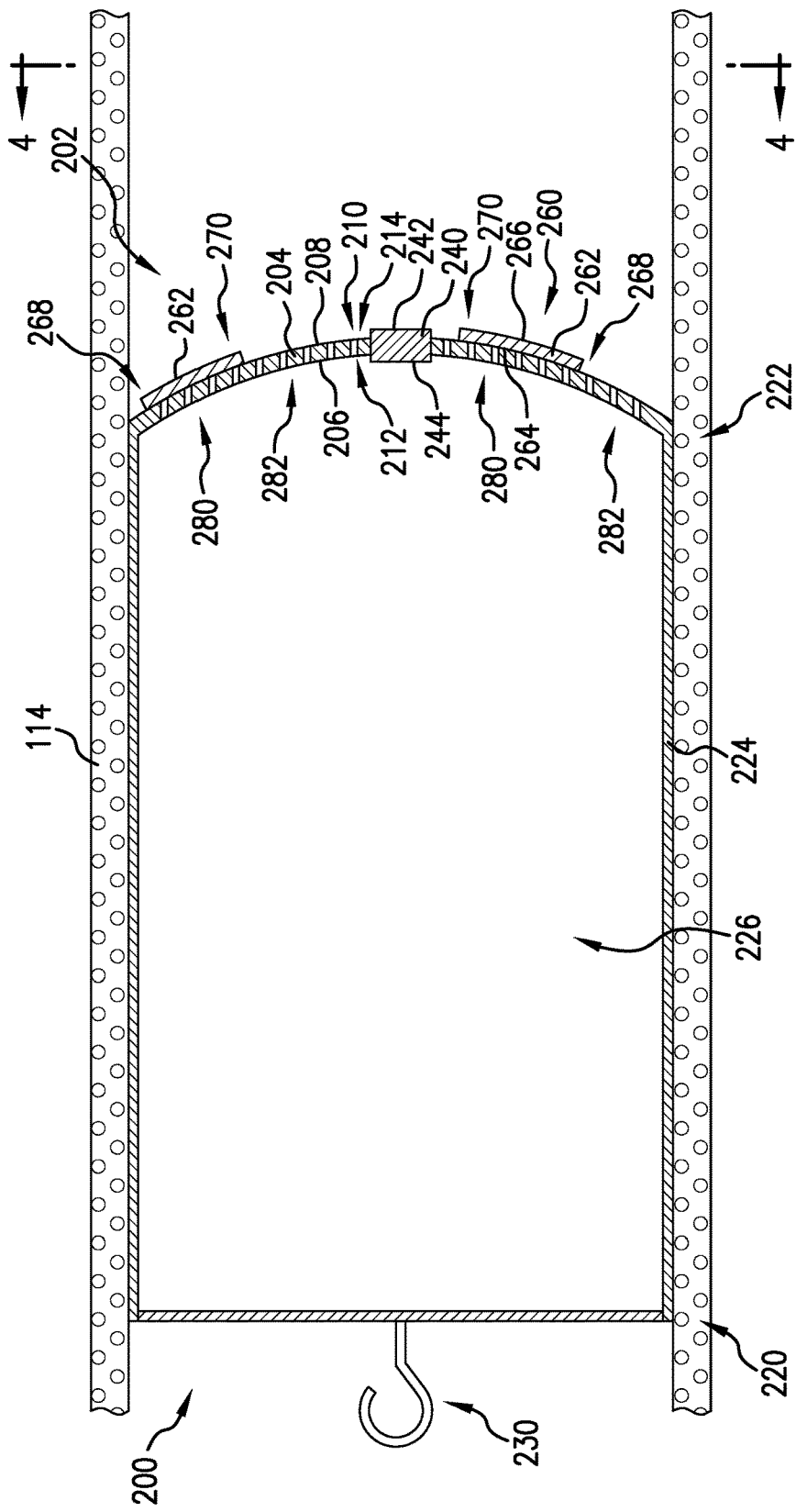
FIG. 2 is a side cross-sectional view of an exemplary implantable device with the valve members in a closed configuration.

FIG. 2 illustrates a cross-sectional view of the implantable device when positioned within a blood vessel of a patient. The implantable device has a filter 202 having a filter element 204 with an upstream side 206 and a downstream side 208. The filter element defines a plurality of filter passageways 210 that extend from a first opening 212 on the upstream side to a second opening 214 on the downstream side. The plurality of filter passageways are sized and configured so as to allow blood to flow through the filter element while preventing emboli that could cause a stroke or transient ischemic attack from passing through the filter element.

The maximum cross-sectional dimension of individual the filter passageways is less than 125 micrometers. For example, the maximum cross-sectional dimension of the filter passageways can be between or including 75 to 100 micrometers. This can be measured as the diameter for filter passageways that have a substantially circular cross-sectional shape. The implantable device can also have a second filter element positioned upstream of filter element 204 and defining a plurality of filter passageways that individually have a maximum cross-sectional dimension of up to or including 5 millimeters. In many instances, the filter passageways of the second filter element have a maximum cross-sectional dimension that is between or including 100 micrometers and 1 millimeter. In this way, the filter elements prevent emboli having a dimension larger than the filter passageway from passing downstream.

The filter element is fitted to the target artery size and can have a maximum cross-sectional dimension between or including 4 millimeters to 15 millimeters. In many instances, the filter element has a maximum cross-sectional dimension between or including 10 and 12 millimeters. For example, for an implantable device arranged for implantation into the common carotid artery, a preferred cross-sectional dimension is 11 millimeters. For implantable devices arranged for implantation into the external or internal carotid arteries, a preferred maximum cross-sectional dimension is 6 millimeters.

The implantable device has an upstream end 220 and a downstream end 222 with distal filter element 204 being positioned at the downstream end. A sidewall 224 extends between the upstream end and the downstream end of the implantable device and defines an inner cavity 226. Positioned at the upstream (e.g., proximal) end of the implantable device is a retrieval hook 230 that is arranged and useful for deploying and retrieving the implantable device.

Coupled to the filter is a pressure sensor 240. The pressure sensor has a downstream side 242 that, when implanted into the blood vessel of a patient, is in fluid communication with blood that is adjacent to the downstream side of the filter element. In this way, the pressure sensor can measure the pressure of the blood on the downstream side of the filter element.

In some instances, the pressure sensor is a differential sensor and has an upstream side 244 that is in fluid communication with blood that is adjacent to the upstream side of the filter element. In this way, the pressure sensor can output a signal that is representative of the difference in fluid pressure between the fluid on the upstream side of the filter element and the downstream side of the filter element.

Also coupled to the filter is a valve 260 that includes a valve member 262 that extends across a portion of the downstream side of the filter element. The valve member has an upstream side 264 that faces the downstream side of the filter element and a downstream side 266 that faces away from the filter element. The upstream and downstream sides of the valve member extend between a first end 268 and a second end 270 with the first end being fixed to the filter element, such as by being fixed to the filter element along an edge 276 with sutures or bonding (e.g., heat or adhesive bonding).

Figure 3:
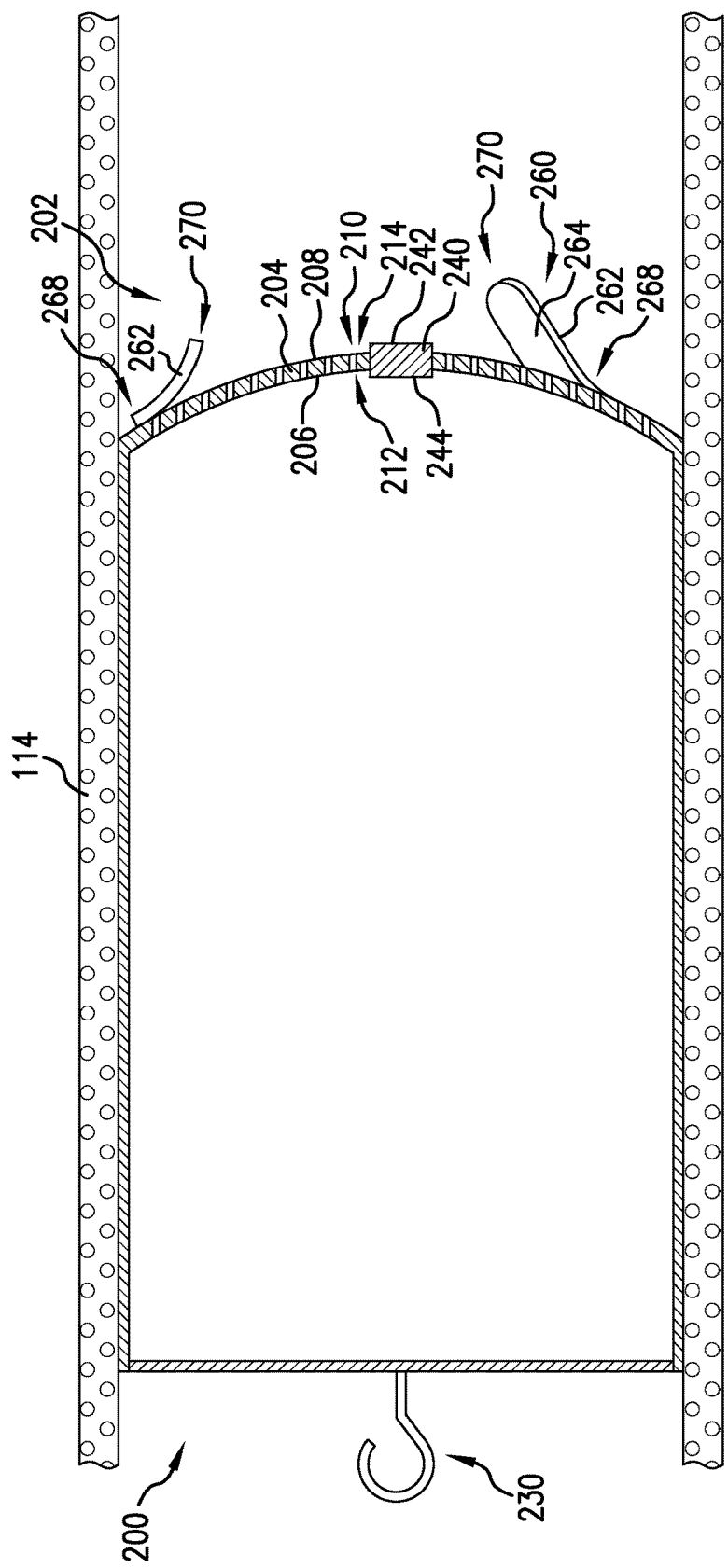
FIG. 3 is a side cross-sectional view of the implantable device of FIG. 2 with the valve members in an open configuration.

The valve member is configurable from a closed configuration (illustrated in FIG. 2) to an open configuration (illustrated in FIG. 3). In the closed configuration, the upstream side of the valve member extends across a portion of the downstream side of the filter element and across the second opening of at least one filter passageway so as to close the second opening of the filter passageway. In this way, the valve member can close at least one filter passageway and resist the flow of fluid (e.g., blood) through the passageway. In the open configuration, the second end of the valve member is pivoted away from the filter element so that the upstream side of the valve member is spaced from the second opening(s) of the filter passageway(s). The valve member, in the open configuration, therefore does not close the second opening(s) of the filter passageway(s) that are covered in the closed configuration. The open configuration, therefore, allows blood to flow through the filter passageway(s) and out of the second opening.

The valve member is biased into the closed configuration by a material property of the valve member or by a biasing member. For example, the valve member may be a resilient member that is biased into the closed configuration by the stiffness of the material(s) of the valve member. In this way, the valve member is configurable from a closed configuration into a deformed open configuration when there is a sufficiently large pressure gradient across the filter element. For example, the valve member can be arranged to move from the closed configuration into the open configuration when the fluid pressure on the upstream side is at least 1300 or 7000 Pascals greater than the fluid pressure on the downstream side of the filter element. In this way, the valve member allows an increase in blood flow and blood pressure on the downstream side of the filter element so as to reduce the likelihood of a blocked or clogged filter element causing a stroke or ischemic event in the brain of the patient.

In the closed configuration, the valve member lies across a portion 280 of the filter element, blocking the second opening of the filter passageways in that portion of the filter element and preventing material from flowing through those filter passageways. Blood therefore flows through the uncovered portions 282 when the valve member is in the closed configuration, with the filter passageways in the uncovered portions filtering and collecting emboli. As the uncovered portions of the filter element become clogged or blocked over time, the pressure difference between the upstream side and downstream side of the filter element will increase and one or more of the valves will configure from the closed configuration into the open configuration (e.g., either partially open or fully open) so as to uncover and expose the second openings of passageways and allow blood to flow through those passages. The valves therefore provide a pressure release for when uncovered portions of the filter element become clogged or blocked, thus allowing additional blood flow downstream of the filter element. Additionally, the valves are arranged so that selected areas of the filter element (i.e., the uncovered portions) become clogged or blocked before other areas (i.e., the covered portions). Advantageously, this arrangement provides an implantable device that can maintain a more precise pressure drop across the filter element over the lifetime of the device as opposed to a traditional filter element that has a continual increase in the pressure drop across the filter element. Additionally, the arrangements disclosed herein provide a visual indication to a medical professional as to the status of the implantable device (e.g., whether the filter element is clogged/blocked) by the valve members being visualizable, such as by x-ray, ultrasound or MRI, relative to the filter and/or filter element so that a medical professional may determine whether the valve member is in a closed configuration, a partially-open configuration, or an open configuration.

Figure 4:
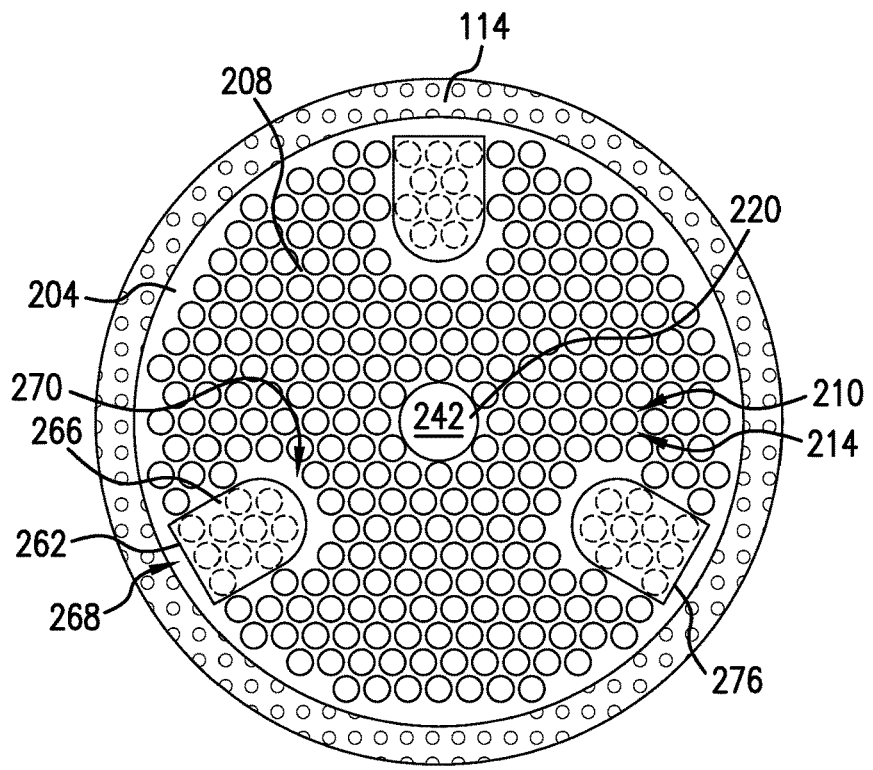
FIG. 4 is an end view of the implantable device of FIG. 2.
Figure 5:
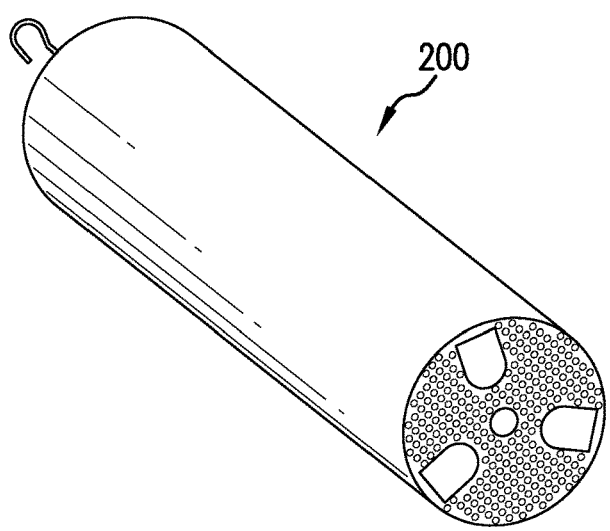
FIG. 5 is a perspective view of the implantable device of FIGS. 2 and 4.

FIG. 4 illustrates an end view of the implantable device in a closed configuration taken along line 4-4 of FIG. 2. The valve members are arranged such that the first and second ends of a valve member lay along a radius of the filter element, with the second end being positioned radially inward relative to the first end. In this arrangement, the valve member pivots (e.g., hinges) around the second end and towards the vessel wall when moving from the closed configuration to the open configuration. The valve members can be spaced equally across the area of the filter element. For example, as illustrated in FIG. 4, the valve members are spread 120° apart from one another around the face of the filter element. FIG. 5 illustrates a perspective view of the implantable device described above.

Referring back to FIG. 1, the implantable device may be part of a system having an external device 320. For example, the pressure sensor of the implantable device can be in wireless communication 300 with an external device 320 such as a cell phone, a personal computer, or a tablet device, just to name a few non-limiting examples. The external device 320 receives a signal representative of the upstream-downstream pressure difference sensed by the pressure sensor. The external device then processes this signal so as to determine a condition of the implantable device. For instances, the external device may determine whether the filter element has become clogged with emboli by, for example, comparing the signal from the pressure sensor of the upstream-downstream pressure difference to a known value, such as a signal representative of a known pressure drop across a clean filter.

The external device can have an alarm, such as a display screen 322 and/or a speaker 324. When the external device determines that the filter element of the implantable device is clogged or significantly impeding blood flow, the external device may trigger an audible alarm and/or display a message on the screen for the patient, such as "Your left carotid artery blood pressure is 10% low! Contact your doctor immediately!"

In patient's having two or more implantable devices, such as implantable device 200, positioned in their arteries, the external device can compare the signals from the implantable devices. For example, if a patient has a first implantable device in the right common carotid artery and a second implantable device in the left common carotid artery, the external device may compare the signals from the first and second implantable devices so as to determine whether one of the filter elements is clogged.

The above embodiment illustrated in the drawings and described in detail is to be considered as illustrative and not restrictive in character. Variations of the above illustrated embodiment are contemplated. In particular, the teachings herein can provide any of the following features, individually or in any combination.

The filter elements can comprise a disc, dome, cylinder, or other three-dimensional shape of material. For example, the filter elements may comprise a mesh or thin perforated sheet. The filter elements are preferably formed of or coated with a biocompatible material so as to minimize or prevent undesirable responses by the body, including inflammation, antibody and platelet attraction or activation. The filter elements can comprise organic or synthetic materials including metals.

The implantable device can include a single filter element or multiple filter elements. In multiple filter element embodiments, the filter elements can be arranged in series along a length of the implantable device such that as blood flows through the implantable device it is sequentially filtered by the separate elements. Multiple filter elements can be spaced from one another (e.g., 1 mm between the filter elements) or the multiple filter elements can be in abutting contact with one another.

Preferably, in the arrangements having multiple filter elements, the filter passageways of a downstream (e.g., distal) filter element are smaller in cross-sectional dimension than the filter passageways of an upstream (e.g., proximal) filter element. In this way, the larger emboli and the smaller emboli flowing in the blood are separated by different filter elements, thus increasing the amount of emboli that the implantable device can filter out of the blood before the most downstream filter element becomes clogged.

The pressure sensor can be attached to the filter element, as illustrated, or connected to the luminal wall of the blood vessel by sutures, barbs, or clips, to name a few non-limiting examples. Additionally, the pressure sensor can be placed in locations other than in the center of the filter element. For example, the pressure sensor can be positioned adjacent the periphery of the filter element or positioned on the sidewall of the implantable device.

The implantable device may include one or more pressure sensors. For example, a differential pressure sensor may be used to measure the pressure difference between the upstream and downstream sides of a filter element. As an alternative example, the implantable device may include a sealed pressure sensor that communicates with fluid upstream or downstream of a filter element so as to measure the pressure of that fluid and then that measurement may be compared with the measurement from another pressure sensor positioned on the same or on a different implantable device.

The implantable device and/or components thereof (e.g., the pressure sensors) can be active, semi-active or passive. For example, an active or semi-active implantable device may include a battery to power the pressure sensor and wireless communication module, such as a radio-frequency ("RF") transmitter. A passive implantable device relies on another device as the power source, using a radio wave, magnetic field or light beam emitted from the other device to power the implantable device. For example, a conductive wire may be positioned along the sidewall 224 and coiled around the inner cavity 226 so as to allow the transcutaneous transfer of electrical power via electromagnetic induction. In some instance, the sidewall 224 comprises the conductive wire. Alternatively, the external device may have a wireless power unit with a radio-frequency transmitter that emits radio waves that are received by a radio-frequency receiver (e.g., an antenna positioned along the sidewall) of the implantable device and used to power the pressure sensor and wireless communication module.

The external device that communicates with the implantable device and receives data from the pressure sensor can be a stationary device; a hand-held device such as a cell phone or hand-held receiver; or it can be a wearable device such as a necklace, an earring, a watch, a bracelet, a hearing aid, or an ornamental pin, just to name a few non-limiting examples. The external device preferably has an alarm that can notify the patient and/or a medical professional of a blocked or clogged filter. For example, the alarm may include a sound emitter such as speaker or piezoelectric element that will buzz. Alternatively or additionally, the alarm may include a light or a screen that provides a visual notification or a vibrator that produces vibrations, just to name a few non-limiting examples. Exemplary notifications that may be emitted from a speaker or displayed on a screen are as follows: "Carotid artery blood pressure OK"; "Your left carotid artery blood pressure is 10% low! Contact doctor XYZ immediately!" For alarms that notify a medical professional, the external device may call or message the patient's doctor. For example, the doctor's cell phone may ring and present a notification of "Your patient, XYZ, has 10% reduced pressure in her left common, carotid artery. She should receive immediate attention!" For treatment, the doctor may decide among a choice of options such as dissolving an embolus such as by using tissue plasminogen activator (tPA), removing the emboli by catheter, or removing the implantable device from the body of the patient.

The external device in combination with the implantable device may be arranged to monitor combinations of systolic and diastolic blood pressure upstream and downstream of the filter elements. Furthermore, the external device may communicate with multiple implantable devices positioned in different arteries so as to compare blood pressure measurements between different arteries. When determining whether a filter element is blocked or clogged, the external device may compare blood pressure measurements from at least one pressure sensor with the measurements from at least one pressure sensor in a different blood vessel or with known values for clean or clogged filters.

The implantable device may have more or fewer valve members that those illustrated in the provided drawings. Additionally, the valve members can be positioned in other locations and in other orientations than those illustrated.

The valve members are arranged so as to open when there is a sufficiently large pressure gradient across the filter element. Preferably, the valve member is arranged to move into the open configuration when there is likelihood that the blocked or clogged filter element may cause a stroke or ischemic event in the brain of the patient. For example, the valve member can be arranged to move from the closed configuration into the open configuration when the fluid pressure on the upstream side is at least 1300 or 7000 Pascals greater than the fluid pressure on the downstream side of the filter element. Alternatively or additionally, a valve member of an implantable device may be arranged so as to remain in the closed configuration during normal blood flow through a clean (i.e., unclogged) filter element but then to move into the open configuration as filter passageways uncovered by the filter element become blocked or clogged so as to provide an indication as to how many of the filter passageways and/or how much of the surface area of the filter element is blocked or clogged by emboli. For example, under normal blood flow conditions, the valve member may be arranged to move from the closed configuration into the open configuration when 50% or more of the filter passageways of surface area of the filter element is blocked or clogged with emboli. Through the use of X-ray or circuitry on the implantable device, the doctor can determine whether the valve member or how many valve members are in the open configuration. This will provide the doctor with an indication of how blocked or clogged the filter element or filter elements of the implantable device are.

Valve members of an implantable device can be of the same or a different, size, shape and/or material. For example, valve members may be constructed from a biocompatible rubber or metal such as nickel-titanium (aka: "nitinol"). Furthermore, valve members of an implantable device may be arranged to move from the closed configuration into the open configuration under different pressure differentials. For example, a first valve member may be arranged to move into the open configuration when the pressure differential is at least 800 Pascals while a second valve member may be arranged to move into the open configuration when the pressure differential is at least 7000 Pascals.

Different types of valve members are suitable. The valve members are preferably of the check valve type which are arranged to open in response to a certain pressure differential across the filter element. The valve members may be a reed valve or a swing valve as illustrated. Alternatively, the valve members can be a duckbill valve, to name just a few non-limiting examples. The valve member can comprise a cut-out portion of the filter element itself, with the cut-out portion hingedly attached to the filter element and arranged to open at a predetermined pressure differential across the filter element. For example, the valve member can comprise a flap of filter element material formed by a semicircular or U-shaped cut in the filter element with an intact (i.e., uncut) portion of the filter element material serving as a hinge for the flap of filter element material.

Portions of the implantable device may be constructed of a radiopaque material and/or have a radiopaque marker attached thereto. For example, the valve members may have a gold wire embedded therein. Alternatively or additional, the valve member or a radiopaque marker attached to the implantable device may comprise at least one of tantalum, barium, tungsten, gold, platinum and/or bismuth, and/or a derivative thereof.

The language used in the claims and the written description and in the above definitions is to only have its plain and ordinary meaning, except for terms explicitly defined above. Such plain and ordinary meaning is defined here as inclusive of consistent dictionary definitions from the most recently published (as of 4 Jun. 2014) Oxford English dictionaries, Webster's dictionaries, or Random House dictionaries.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the devices and systems defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The following numbered clauses set out specific embodiments that may be useful in understanding the present invention:

1. An implantable device for implantation into a blood vessel of a patient, comprising:
 a filter having a first filter element with an upstream side and a downstream side and defining a plurality of filter passageways extending from the upstream side to the downstream side;
 a first pressure sensor coupled to the filter and operable to sense the pressure of blood adjacent to the downstream side when the filter is implanted in a blood vessel; and
 a valve coupled to the filter and configurable from a closed configuration to an open configuration; and
 the valve in the closed configuration closing a passageway that extends from the upstream side of the filter element to a downstream side of the filter element.

2. The implantable device of clause 1, wherein:
 the valve is biased into the closed configuration.

3. The implantable device of clause 1 or 2, wherein:
 the valve comprises a valve member that extends across a portion of the downstream side of the first filter element; and
 wherein in the closed configuration the valve member covers openings of some of the plurality of filter passageways.

4. The implantable device of any preceding clause, wherein:
 the filter has a maximum outer dimension of 4 to 15 millimeters.

5. The implantable device of clause 4, wherein:
 the filter has a maximum outer dimension of 6 millimeters.

6. The implantable device of any preceding clause, wherein:
 the valve comprises a check valve.

7. The implantable device of clause 6, wherein:
 the valve is arranged to move into the open configuration when the fluid pressure on the upstream side is at least 1300 Pascals greater than the fluid pressure on the downstream side of the first filter element.

8. The implantable device of clause 6, wherein:
 the valve is a flap valve.

9. The implantable device of clause 6, wherein:
 the valve is a duckbill valve.

10. The implantable device of any one of the above clauses, wherein:
 the first pressure sensor is a differential pressure sensor that is also in communication with fluid adjacent to the upstream side of the filter element when the filter element is implanted in a patient so that the first pressure sensor outputs a signal that corresponds to the pressure difference between fluid adjacent the upstream side and fluid adjacent the downstream side of the filter element.

11. The implantable device of any one of clauses 1 to 9, further comprising:
 a second pressure sensor coupled to the first filter element and in communication with fluid adjacent to the upstream side of the first filter element; and
 wherein the first and second pressure sensors are sealed pressure sensors and measure pressure of within the blood vessel relative to a fixed pressure within the sensor.

12. A system, comprising:
 a first implantable device comprising the implantable device of any one of the above clauses; and
 an external device in wireless communication with the first pressure sensor of the first implantable device.

13. The system of clause 12, further comprising:
 a second implantable device comprising the implantable device of any one of clauses 1 to 10; and
 wherein the external device is in wireless communication with the first pressure sensor of the second implantable device.

14. The system of clause 12 or 13, wherein:
 the external device comprises one or more alarms triggerable by at least a signal output of the first pressure sensor of the first implantable device or by at least a signal output of the first pressure sensor of the second implantable device.

15. The system of any one of clauses 12 to 14, wherein:
 the external device has a wireless power unit arranged to power at least the first implantable device.

16. The system of clause 15, wherein:
 the wireless power unit comprises a radio-frequency transmitter; and
 the first implantable device comprises a radio-frequency receiver.

17. The system of clause 15, wherein:
 the wireless power unit comprises a light source; and
 the first implantable device comprises a light receiver.

18. An implantable device for implantation into a blood vessel of a patient, comprising:

a filter having a first filter element with an upstream side and a downstream side and defining a plurality of filter passageways extending from the upstream side to the downstream side; and a valve coupled to the filter and configurable from a closed configuration to an open configuration;

wherein the valve has a valve member comprising a first visualizable marker;

wherein the filter has a second visualizable marker; and wherein the first visualizable marker is displaced relative to the second visualizable marker when the valve is in the open configuration so as to indicate that the valve is in the open configuration.

What is claimed is:

1. An implantable device for implantation into a blood vessel of a patient, comprising:
    a filter having a first filter element with an upstream side and a downstream side and defining a plurality of filter passageways extending from the upstream side to the downstream side;
    a first pressure sensor coupled to the filter and operable to sense the pressure of blood adjacent to the downstream side when the filter is implanted in a blood vessel; and
    a valve coupled to the filter and configurable from a closed configuration to an open configuration; and
    the valve in the closed configuration closing a passageway that extends from the upstream side of the filter element to a downstream side of the filter element;
    wherein the valve is arranged to configure from the closed configuration into the open configuration in response to an increase in pressure difference between the upstream side and downstream side of the filter element due to portions of the filter element becoming clogged or blocked in the blood vessel; and
    wherein the first filter element is configured to be disposed along a radial direction between walls of the blood vessel.

2. The implantable device of claim 1, wherein:
the valve is biased into the closed configuration.

3. The implantable device of claim 2, wherein:
the valve comprises a valve member that extends across a portion of the downstream side of the first filter element; and
wherein in the closed configuration the valve member covers openings of some of the plurality of filter passageways.

4. The implantable device of claim 2, wherein:
the valve comprises a check valve.

5. The implantable device of claim 1, wherein:
the valve comprises a valve member that extends across a portion of the downstream side of the first filter element; and
wherein in the closed configuration the valve member covers openings of some of the plurality of filter passageways.

6. The implantable device of claim 1, wherein:
the filter has a maximum outer dimension of 4 to 15 millimeters.

7. The implantable device of claim 6, wherein:
the filter has a maximum outer dimension of 6 millimeters.

8. The implantable device of claim 1, wherein:
the valve comprises a check valve.

9. The implantable device of claim 8, wherein:
the valve is arranged to move into the open configuration when the fluid pressure on the upstream side is at least 1300 Pascals greater than the fluid pressure on the downstream side of the first filter element.

10. The implantable device of claim 8, wherein:
the valve is a flap valve.

11. The implantable device of claim 8, wherein:
the valve is a duckbill valve.

12. The implantable device of claim 1, wherein:
the first pressure sensor is a differential pressure sensor that is also in communication with fluid adjacent to the upstream side of the filter element when the filter element is implanted in a patient so that the first pressure sensor outputs a signal that corresponds to the pressure difference between fluid adjacent the upstream side and fluid adjacent the downstream side of the filter element.

13. The implantable device of claim 1, further comprising:
    a second pressure sensor coupled to the first filter element and in communication with fluid adjacent to the upstream side of the first filter element; and
    wherein the first and second pressure sensors are sealed pressure sensors and measure pressure of within the blood vessel relative to a fixed pressure within the sensor.

14. The implantable device of claim 1 comprising:
wherein the valve has a valve member comprising a first radiopaque visualizable marker;
wherein the filter has a second radiopaque visualizable marker; and
wherein the first radiopaque visualizable marker is displaced relative to the second radiopaque visualizable marker when the valve is in the open configuration so as to indicate that the valve is in the open configuration.

15. A system, comprising:
    a first implantable device comprising the implantable device of claim 1; and
    an external device in wireless communication with the first pressure sensor of the first implantable device.

16. The system of claim 15, further comprising:
    a second implantable device comprising the implantable device of claim 1; and
    wherein the external device is in wireless communication with the first pressure sensor of the second implantable device.

17. The system of claim 16, wherein:
the external device comprises one or more alarms triggerable by at least a signal output of the first pressure sensor of the first implantable device or by at least a signal output of the first pressure sensor of the second implantable device.

18. The system of claim 15, wherein:
the external device has a wireless power unit arranged to power at least the first implantable device.

19. The system of claim 18, wherein:
the wireless power unit comprises a radio-frequency transmitter; and
the first implantable device comprises a radio-frequency receiver.

20. The system of claim 18, wherein:
the wireless power unit comprises a light source; and
the first implantable device comprises a light receiver.

21. An implantable device for implantation into a blood vessel of a patient, comprising:
    a filter having a first filter element with an upstream side and a downstream side and defining a plurality of filter passageways extending from the upstream side to the downstream side;

a first pressure sensor coupled to the filter and operable to sense the pressure of blood adjacent to the downstream side when the filter is implanted in a blood vessel; and a valve coupled to the filter and configurable from a closed configuration to an open configuration; and the valve in the closed configuration closing a passageway that extends from the upstream side of the filter element to a downstream side of the filter element;

wherein the valve comprises a valve member that extends across a portion of the downstream side of the first filter element; and wherein in the closed configuration the valve member covers openings of at least two of the plurality of filter passageways.

* * * * *